US011426395B2

(12) United States Patent
Sikora et al.

(10) Patent No.: US 11,426,395 B2
(45) Date of Patent: Aug. 30, 2022

(54) PSMA INHIBITOR DERIVATIVES FOR LABELLING WITH 99MTC VIA HYNIC, A RADIOPHARMACEUTICAL KIT, RADIOPHARMACEUTICAL PREPARATIONS AND THEIR USE IN PROSTATE CANCER DIAGNOSTICS

(71) Applicant: Narodowe Centrum Badan Jadrowych, Osrodek Radioizotopow POLATOM, Otwock-Swierk (PL)

(72) Inventors: Arkadiusz Eugeniusz Sikora, Gorlice (PL); Michal Maurin, Warsaw (PL); Antoni Wlodzimierz Jaron, Izabelin (PL); Justyna Pijarowska-Kruszyna, Warsaw (PL); Monika Wyczólkowska, Warsaw (PL); Barbara Janota, Warsaw (PL); Marcin Radzik, Warsaw (PL); Piotr Garnuszek, Warsaw (PL); Urszula Karczmarczyk, Otwock (PL)

(73) Assignee: NARODOWE CENTRUM BADAN JADROWYCH, OSRODEK RADIOIZOTOPOW POLATOM, Otwock-Swierk (PL)

( * ) Notice: Subject to any disclaimer, the term of this patent is extended or adjusted under 35 U.S.C. 154(b) by 0 days.

(21) Appl. No.: 16/559,014

(22) Filed: Sep. 3, 2019

(65) Prior Publication Data
US 2020/0324000 A1  Oct. 15, 2020

(30) Foreign Application Priority Data

Apr. 12, 2019 (PL) ........................................ 429630

(51) Int. Cl.
| | | |
|---|---|---|
| A61K 31/4439 | (2006.01) | |
| A61K 51/04 | (2006.01) | |
| A61P 35/00 | (2006.01) | |
| A61K 9/19 | (2006.01) | |
| A61K 31/404 | (2006.01) | |

(52) U.S. Cl.
CPC ............ *A61K 31/4439* (2013.01); *A61K 9/19* (2013.01); *A61K 31/404* (2013.01); *A61K 51/0402* (2013.01); *A61K 51/0446* (2013.01); *A61K 51/0455* (2013.01); *A61K 51/0497* (2013.01); *A61P 35/00* (2018.01)

(58) Field of Classification Search
None
See application file for complete search history.

(56) References Cited

FOREIGN PATENT DOCUMENTS

| CA | 3059545 A1 | 12/2017 |
|---|---|---|
| WO | 2010/014933 A2 | 2/2010 |
| WO | 2010014933 A2 | 2/2010 |

OTHER PUBLICATIONS

Ferro-Flores et al., "Clinical translation of a PSMA inhibitor for 99mTc-based SPECT", Nuclear Medicine and Biology, May 1, 2017, vol. 48, pp. 36-44, Elsevier.
Godlewski, Piotor, Extended European Search Report, dated Apr. 24, 2020, European Patent Office, Germany.
Ferro-Flores Guillermina et al: "Clinical Translation of a PSMA Inhibitor for99MTC-Based Spect", Nuclear Medicine and Biology, Elsevier, NY, US, vol. 48, Feb. 3, 2017 (Feb. 3, 2017), pp. 36-44, XP029963241, ISSN: 0969-8051, DOI: 10.1016/J.NUCMEDBIO. 2017.01.012* p. 37, Last Paragraph of Introduction and Paragraph 2.2; p. 38, Paragraph 2.6.1.1; Figure 1A.
Sangeeta Ray Banerjee et al: "Effect of Chelators on the Pharmacokinetics of 99M TC-Labeled Imaging Agents for the Prostate-Specific Membrane Antigen (PSMA)", Journal of Medicinal Chemistry, vol. 56, No. 15, Aug. 8, 2013 (Aug. 8, 2013), pp. 6108-6121, XP055280715, US ISSN: 0022-2623, DOI: 10.1021/JM400823W.
Xu Xiaoping et al: 99MTC-Labeling and Evaluation of a HYNIC Modified Small-Molecular Inhibitor of Prostate-Specific Membrane Antigen, Nuclear Medicine and Biology, Elsevier, MY, US, vol. 48, Jan. 28, 2017 (Jan. 28, 2017), pp. 69-75, XP029963281, ISSN: 0969-8051, DOI: 10.1016/J.NUCMEDBIO.2017.01.010.
Hernandez-Jimenez Tania et al: "177LU-DOTA-HYNIC-LYS(NAL)-UREA-GLU: Synthesis and Assessment of the Ability to Target the Prostate Specific Membrane Antigen", Journal of Radioanalytical and Nuclear Chemistry, Akademiai Kiado RT, HU, vol. 318, No. 3, Oct. 9, 2018 (Oct. 9, 2018), pp. 2059-2066, XP036649215, ISSN: 0236-5731, DOI: 10.1007/S10967-018-6239-9 [Retrieved on Oct. 9, 2018].
Clara Santos-Cuevas et al: "177 LU-DOTA-HYNIC-LYS(NAL)-UREA-GLU: Biokinetics, Dosimetry, and Evaluation in Patients With Advanced Prostate Cancer", Contrast Media & Molecular Imaging, vol. 2018, Nov. 11, 2018 (Nov. 11, 2018), pp. 1-10, XP055685809, GB ISSN: 1555-4309, DOI: 10.1155/2018/5247153.
European Search Report, Application No. EP 19 19 9838, Place of Search: The Hague, Date of Completion of the Search: Apr. 16, 2020.
Search Report, Urzad Patentowy, Pzeczypospolitej Polskiej, Sprawozdanie O Stanie Techniki Zgloszenia NR p. 429630, Data 22.01.2020R.
Shawn Hillier, et al., "TC-99M-Labeled Small Molecule Inhibitors of Prostate-Specific Membrane Antigen for Molecular Imaging of Prostate Cancer", Journal of Nuclear Medicine 54(8), Jun. 2013.
https://open.library.ubc.ca/cIRcle/collections/ubctheses/24/items/1.0364201, Spreckelmeyer, Sarah, "Metallodrugs for Therapy and Imaging: Investigation of Their Mechanism of Action", Vancouver: University of British Columbia, Mar. 31, 2019.
Sweat SD, Pacelli A, Murphy GP, Bostwick DG Prostate-specific membrane antigen expression is greatest in prostate adenocarcinoma and lymph node metastases. Urology. 1998;52(4):637-40.

(Continued)

*Primary Examiner* — Jennifer Lamberski
(74) *Attorney, Agent, or Firm* — Flener IP & Business Law; Zareefa B. Flener (57) ABSTRACT

The subject matter of the invention is PSMA inhibitor-HYNIC derivatives of PSMA-L$_1$-L$_2$-HYNIC formula, aromatic and aliphatic hydrazone derivatives, a radiopharmaceutical kit for 99mTc isotope labelling, radiopharmaceutical preparation and its application for prostate cancer and its metastasis diagnostics.

6 Claims, 2 Drawing Sheets

(56) References Cited

OTHER PUBLICATIONS

Banerjee SR, Foss CA, Castanares M, et al. Synthesis and evaluation of technetium-99m- and rhenium-labeled inhibitors of the prostate-specific membrane antigen (PSMA). J Med Chem. 2008;51:4504-4517.

Kularatne SA, Zhou Z, Yang J, Post CB, Low PS. Design, synthesis, and preclinical evaluation of prostate-specific membrane antigen targeted 99mTc-radioimaging agents. Mol Pharm. 2009;6:790-800.

Robu S, Schottelius M, Eiber M, Maurer T, Gschwend J, Schwaiger M, Wester HJ. Preclinical Evaluation and First Patient Application of 99mTc-PSMA-I&S for SPECT Imaging and Radioguided Surgery in Prostate Cancer. J Nucl Med. 2017;58(2):235-242.

Chan W. C., White P.D. Fmoc Solid Phase Peptide Synthesis. A practical approach. 2004, 47-48, 51.

El-Faham A., Albericio F., COMU: A third generation of uranium-type coupling reagents. Journal of Peptide Science. 2010, 16: 6-9.

Subiros-Funosas R., L. Nieto-Rodriguez L., Jensen K. J., Albericio F., COMU: scope and limitations of the latest Innovation in peptide acyl transfer reagents. Journal of Peptide Science. 2010, 16: 408-414.

PSMA INHIBITOR DERIVATIVES FOR LABELLING WITH 99MTC VIA HYNIC, A RADIOPHARMACEUTICAL KIT, RADIOPHARMACEUTICAL PREPARATIONS AND THEIR USE IN PROSTATE CANCER DIAGNOSTICS

The invention relates to new PSMA (Prostate-Specific Membrane Antigen) inhibitor derivatives adapted to labelling with $^{99m}$Tc radionuclide, pharmaceutical formulations in the form of radiopharmaceutical kits for preparing pharmaceutical preparations labelled with $^{99m}$Tc, pharmaceutical preparations and their use in prostate cancer and its metastasis diagnostics.

Prostate cancer is one of the most frequently occurring neoplasms in men. Nowadays, early diagnostics and therapy are possible owing to radioisotope markers, such as PSMA inhibitor analogues. Prostate-specific membrane antigen (PSMA) is expressed mainly in normal glandular epithelial cells and its levels increase in prostate cancer, including metastatic disease. Due to the fact that PSMA overexpression is observed practically for all types of prostate cancer and its expression is still increased in poorly differentiated, metastatic and hormone-resistant malignant carcinomas [1], it is an attractive molecular target to develop radiopharmaceuticals for primary and metastatic prostate cancer detection, stage of progression assessment and treatment of the disease.

In recent years, extensive studies have been carried out on the specific PSMA inhibitors having high affinity to prostate cancer cells, which after labelling with an appropriate radioisotope, can be used in diagnostics or therapy. The recently marketed $^{68}$Ga-PSMA-11 tracer for Positron Emission Tomography (PET) appeared extremely useful in prostate cancer metastasis diagnostics and aroused great interest in the use of other PSMA inhibitor analogues.

Despite the fact that in recent years the interest in PET diagnostic procedures has significantly increased, the SPECT method using radiopharmaceuticals labelled with Technetium-99m ($^{99m}$Tc) still accounts for the vast majority of nuclear medicine procedures (>85%). Technetium-99m is the most popular diagnostic radionuclide, which results from its physical properties ($T_{1/2}$ 6.01 h, E$\gamma$ 141 keV), availability ($^{99}$Mo/$^{99m}$Tc generators), rich coordination chemistry and its low radiotoxicity.

A few publications concerning the PSMA inhibitors labelled with $^{99m}$Tc containing in their structure a carbonyl system for radionuclide bonding were released already over 10 years ago [2,3]. However, described preparations had some disadvantages, such as slow pharmacokinetics, high liver uptake, slow clearance in the gastrointestinal tract, which can disrupt their application in prostate cancer imaging because this type of cancer most frequently metastasizes in the lower part of the spine, pelvis and lymph nodes within the abdomen. Therefore, the priority was to develop PSMA inhibitors labelled with $^{99m}$Tc of improved biodistribution and pharmacokinetics. In recent years, many PSMA inhibitor analogues containing technetium-99m chelating systems of N4 or HYNIC type have been created, the presence of which significantly decreased the lipophilicity of the radiolabelled preparations [4-6]. On the other hand, according to the published biodistribution data [4,5] and on the basis of the results of our studies given in Example 6, the developed preparations exhibit very high accumulation in kidneys, which can cause difficulties in the interpretation of scintigraphic images. An additional disadvantage of the already known PSMA derivatives containing HYNIC as a chelator in their structure is limited stability of these compounds. Free hydrazine group present in HYNIC bioconjugates is highly susceptible to oxidation reactions and, as a strong nucleophile, is able to react with compounds with electrophilic properties. Such undesirable reactions lead to the formation of different by-products. It causes great difficulties in purification, reduces purity during freeze-drying, significantly lowers synthesis yield and reduces the stability of prepared kits.

Patent application CA2924360A1 discloses the compound in which the chelator is, among others, DOTA, instead of HYNIC. The document discloses the complex comprising the aforementioned compound and a radionuclide in the form of $^{99m}$Tc as well as a pharmaceutical composition of that complex or its pharmaceutically acceptable salt and pharmaceutically acceptable carrier. Also disclosed is the application of the compound or its complex in the method of patient imaging and diagnostics of prostate cancer and/or its metastasis.

The publication of international patent application WO2017/222362A1 discloses the radiopharmaceutical compound $^{99m}$Tc-EDDA/HYNIC-iPSMA comprising HYNIC as a chelator and iPSMA moiety, but comprising linkers other than those in the compound according to the invention. In addition, *Nuclear Medicine and Biology* 48 (2017) 69-75 discloses the compound comprising HYNIC and linkers which are different from those comprised in compound of the invention and which can be used in prostate cancer detection with SPECT method.

Another example is the compound disclosed in *J Nucl Med* 2015; 56:914-920. It consists of Glu(urea)Lys residue, DOTA chelator able to complex $^{68}$Ga and $^{177}$Lu, and linker comprising 4-aminomethylcyclohexanecarboxylic acid moiety.

The subject matter of the invention is PSMA inhibitor-HYNIC derivatives represented by general formula 1:

Formula 1

(PSMA-L$_1$——L$_2$-HYNIC)

wherein: $L_1$=L-Trp, L-2NaI, a $L_2$=6Ahx, 4Amc
and their pharmaceutically acceptable salts or esters.

The subject matter of the invention is the derivatives of the above-mentioned compounds represented by general formula 1 being the aliphatic hydrazone derivatives of general formula 2:

(PSMA-$L_1$——$L_2$-HYNIC-aliphatic hydrazone)

Formula 2 wherein:
$L_1$=L-Trp, L-2NaI; $L_2$=6Ahx, 4Amc;
R=H, $CH_3$, $(CH_2)_nCH_3$, $(CH_2)_nCH_2OH$, $(CH_2)_nCH_2NO_2$, $(CH_2)_nCH_2N(CH_3)_2$, $(CH_2)_nCH_2X$, $(CH_2)_nCHO$, $CHOCH_3$, $(CH_2)_nCHOCH_3$
X=Cl, Br, I, F
and their pharmaceutically acceptable salts or esters.

The subject matter of the invention is the derivatives of the compounds represented by general formula 1 being the aromatic hydrazone derivatives of general formula 3:

(PSMA-$L_1$——$L_2$-HYNIC-aromatic hydrazone)

Formula 3 wherein:
$L_1$=L-Trp, L-2NaI; $L_2$=6Ahx, 4Amc
R=$R^1$, $R^2$, $R^3$, $R^4$, $R^5$=H, X, $CH_3$, $(CH_2)_nCH_3$, $OCH_3$, $O(CH_2)_nCH_3$, OH, $NO_2$, $NHCH_3$, $N(CH_3)_2$, $(CH_2)_nNCH_3$, $(CH_2)_nN(CH_3)_2$, $CF_3$, $OCF_3$, $SCH_3$, $SO_3Na$, $SO_3K$, $SO_2CH_3$, COOH, COONa, COOK, $(CH_2)_nCOOH$, $(CH_2)_nCOONa$, $(CH_2)_nCOOK$, CN
X=Cl, Br, I, F
and their pharmaceutically acceptable salts or esters.

The subject matter of the invention is also a radiopharmaceutical preparation which has been prepared from one of the said compounds via chemical bonding with 99mTc isotope.

A further subject matter of the invention is a radiopharmaceutical kit intended for labelling with 99mTc isotope characterized in that it contains one of the compounds mentioned above and excipients.

Preferably, the kit is sterile lyophilisate placed in inert gas atmosphere.

Preferably, the kit is characterized in that the excipients are chosen from the group comprising tin(II) chloride, tricine, ethylenediaminediacetic acid (EDDA) and buffer agents.

Further, the subject matter of the invention is the application of the derivatives described above in prostate cancer and its metastasis scintigraphy diagnostics.

As it has been mentioned above, the subject matter of the invention is new molecules targeted to specific PSMA bonding and comprising hydrazine nicotinamide (HYNIC) as a chelating agent for radioactive metal 99mTc, in which the ethylenediaminediacetic acid or tricine are used to complement the metal coordination sphere, characterised in that the chain bonding the biologically active part Glu-CO-Lys and part of chelate system $^{99m}$Tc-EDDA/HYNIC comprises tryptophan (LTrp) or naphtylalanine (L2NaI) molecules, which cause an increase in the lipophilicity and a decrease in the uptake of labelled preparation in kidneys.

The advantage of the molecules according to the invention is that they are easy to transform into hydrazone derivatives, which are compounds of higher stability and thus they are easier to purify and store. The additional advantage is that the hydrazones formed as a result of hydrazine protection reaction exhibit high absorption in the visible light spectrum caused by the presence of conjugated double bonds chromophoric system and additional auxochrome substituent in the aromatic ring. It allows for easier separation and purification using column chromatography. Such a synthetic approach results in the increase of yield by 20-30% and accelerates the production cycle, which is crucial in terms of preparation of the compounds according to the invention.

A significant advantage is that the HYNIC-hydrazone moiety can be very efficiently, directly labelled with Technetium-99m without the necessity of prior deprotection of the hydrazine group susceptible to side reactions. Under given labelling conditions, hydrazone bond is hydrolysed.

In radiopharmacy, the preparation of required ingredients in the form of lyophilized kits for labelling, which can be further labelled with the radionuclide obtained from radionuclide generators, e.g. $^{99}Mo/^{99m}Tc$ generators, is a common practice. It facilitates efficient preparation of the radiopharmaceutical in the hospital radiopharmacy directly before it is administered to the patient.

The aim of the invention is to provide a new specific radiopharmaceutical in the form of a radiopharmaceutical kit for application in the detection of carcinomas that exhibit PSMA overexpression using SPECT technique and having appropriate biodistribution and pharmacokinetics in terms of imaging quality and radiotoxicity.

EMBODIMENTS

The invention has been illustrated with the following embodiments, which are not intended to limit the scope of the invention.

New PSMA inhibitors comprising HYNIC as a chelator and tryptophane or naphtylalanine as lipophilicity modifying linkers have been synthesized on solid phase, whose preparation has been described in Example 1, while the synthesis of HYNIC-PSMA conjugates with free hydrazine group has been described in Example 2. The synthesis and purification method for the compounds according to the invention via transformation into HYNIC-PSMA hydrazone have been described in Example 3. Example 4 describes the preparation of the radiopharmaceutical kit for preparation of $^{99m}Tc$-HYNIC-PSMA comprising one of the PSMA inhibitors according to the invention, tin(II) chloride as a reducing agent, buffer agents and co-ligands for Technetium-99m such as tricine and EDDA. Examples 5 and 6 show the results of comparative in vitro and in vivo studies on new compounds according to the invention as compared to other preparations used in prostate cancer diagnostics, while Example 7 shows the results of preliminary SPECT studies on patients with prostate cancer using $^{99m}Tc$-HYNIC-PSMA according to the invention.

Example 1. Preparation of Glu(tBu)-Urea-Lys-NH$_2$ Resin Support

The synthesis of the substance was carried out on solid phase being Wang polystyrene support, which is used in peptide synthesis.

Fmoc-L-Lys(Alloc) was attached to hydroxyl groups in the support in the manner described previously [7].

7
-continued

8
-continued

After the reaction had been completed, the support was washed with: N,N-dimethylformamide, 50% N,N-dimethylformamide solution in dichloromethane, dichloromethane and dried in vacuum.

-continued

Double molar excess of triphosgene in dry dichloromethane was cooled in dry-ice bath to ≤−50° C. The solution of L-Glu(tBu)OtBu*HCl 0.75% N,N-diisopropylethylamine in dry dichloromethane was prepared separately using sixfold molar excess. The solution was slowly added dropwise into triphosgene solution with stirring so that the temperature would not exceed −50° C. After dropping had been completed, the bath was removed and the solution was stirred until it reached room temperature. To the so obtained isocyanate solution, the dried resin with L-Lys(Alloc) was added and the mixture was stirred for 3 days. The resin was filtered, washed with dichloromethane and dried in vacuum.

The Alloc detachment reaction was carried out in darkness. In the vessel made of dark glass, Pd[P(Ph)$_3$]$_4$(tetrakis(triphenylphosphine)palladium(0)) catalyst was dissolved in 10% morpholine solution in dry dichloromethane in molar ratio of 0.1. The swollen resin was stirred for 3 hours in the previously prepared solution. The resin was filtered and washed with: N,N-dimethylformamide, 2% N,N-diisopropylethylamine solution in N,N-dimethylformamide, 20 mg/ml sodium diethylthiocarbamate in N,N-dimethylformamide, N,N-dimethylformamide and dichloromethane and then dried in vacuum.

Example 2. Synthesis of PSMA-T4 (PSMA-LTrp-4Amc-HYNIC)

Polystyrene Wang resin with Glu(tBu)-urea-Lys-NH2 was used in the reaction. To the free amine group of Lysine, the Fmoc-L-Trp(Boc) was attached using 1-[(1-(cyano-2-ethoxy-2-oxoethylideneaminooxy)dimethylaminemorpholino)]uronium hexafluorophosphate (COMU) in the manner described previously [8,9]. The resin was placed in a vessel for peptide synthesis and swollen by stirring with dichloromethane. In a separate vessel, threefold molar excess of Fmoc-L-Trp(Boc), threefold molar excess of COMU and N,N-dimethylformamide were placed and stirred until dissolved. Then N,N-diisopropylethylamine was added and stirred for 5 minutes. Dichloromethane was added and stirred. The activated amino acid solution prepared in such a manner was transferred to the vessel with swollen resin and stirred for 1 hour. The resin was washed with: N,N-dimethylformamide, 50% N,N-dimethylformamide solution in dichloromethane and dichloromethane.

The Fmoc protection group was removed in the manner usually used in peptide synthesis [10]. To the vessel with swollen resin, 20% piperidine solution in N,N-dimethylformamide was poured and stirred for 30 minutes After that time, pyridine solution was changed for the fresh one and the mixture was stirred for another 30 minutes. The resin was washed with: N,N-dimethylformamide, 50% N,N-dimethylformamide solution in dichloromethane and at the end with dichloromethane.

molar excess of COMU and N,N-dimethylformamide were placed in a separate vessel and stirred until dissolved. Then N,N-diisopropylethylamine was added and stirred for 5 minutes. Dichloromethane was added and stirred. The activated amino acid solution prepared in such a way was transferred into the vessel with the swollen resin and stirred

Fmoc-4Amc attachment and detachment of the Fmoc protection group were carried out in the manner analogous to the one used in the previous synthetic step. The resin was swollen by stirring in dichloromethane for at least 20 minutes. Threefold molar excess of Fmoc-4Amc, threefold for 1 hour. The support was washed with: N,N-dimethylformamide, 50% N,N-dimethylformamide solution in dichloromethane and, finally, with dichloromethane.

To the vessel with swollen support, 20% piperidine solution in N,N-dimethylformamide was poured and stirred for

30 minutes After that time, piperidine solution was changed for the fresh one and the mixture was stirred for another 30 minutes. The resin was washed with: N,N-dimethylformamide, 50% N,N-dimethylformamide solution in dichloromethane and dichloromethane.

and N,N-dimethylformamide were placed in a separate vessel and stirred until dissolved. Then N,N-diisopropylethylamine was added and stirred for 5 minutes. Dichloromethane was added and stirred. The solution of activated amino acid prepared in such a way was transferred into the vessel HYNIC-Boc attachment was carried out in the manner analogous to the one used in the previous synthetic step, but with longer reaction time. The resin was swollen by stirring in dichloromethane for at least 20 minutes. Threefold molar excess of HYNIC-Boc, threefold molar excess of COMU with swollen resin and stirred for 2 hours. The resin was washed with: N,N-dimethylformamide, 50% N,N-dimethylformamide solution in dichloromethane and with dichloromethane and dried in vacuum.

In a separate vessel, the solution of trifluoroacetic acid with addition of triisopropylsilane, phenol, thioanisole, water and 1,2-ethanedithiole was prepared in order to detach the product from the resin and to remove the protection groups. The ready solution was transferred to the vessel comprising the resin and stirred for 3 hours. The product was precipitated with diethyl ether. The precipitate was centrifuged and washed with diethyl ether. After it had been dissolved in 0.1% trifluoroacetic acid solution, it was heated on a vacuum evaporator up to 60° C. at 800 mbar for 1 hour. The obtained solution was lyophilized.

The lyophilized product was dissolved in acetonitrile/water solvent mixture with addition of 0.1% trifluoroacetic acid and then purified on a preparative polymeric HPLC reversed phase column. Collected fractions containing the compound (PSMA-T4) fulfilling the purity requirements were combined and lyophilized.

In the way analogous to PSMA-T4, the following combinations were obtained:

PSMA-NaI-Amc-HYNIC (PSMA T1) using Fmoc-L2NaI instead of Fmoc-LTrp.

PSMA-NaI-6Ahx-HYNIC (PSMA-T2) using Fmoc-L2NaI instead of Fmoc-LTrp.

PSMA-LTrp-6Ahx-HYNIC (PSMA-T3) using Fmoc-6Ahx instead of Fmoc-4Amc.

TABLE 1

Physicochemical data of PSMA-T1, PSMA-T2, PSMA-T3, PSMA-T4 compounds.

| Compound | Molecular formula; MW; MS: m/z | Solubility according to Ph. Eur. | Form | HPLC purity |
|---|---|---|---|---|
| PSMA-T1 | $C_{39}H_{50}N_8O_{10}$; 790.86 g/mol; m/z = 791.37[M + H]$^+$ | water: slightly soluble pH 7.4 phosphte buffer: very slightly soluble ethanol: soluble | White lyophilisate | ≥97.0% |
| PSMA-T2 | $C_{35}H_{47}N_9O_{10}$; 764.34 g/mol; m/z = 755.35[M + H]$^+$ | water: practicaly insoluble pH 7.4 phosphte buffer: very slightly ethanol: soluble | White lyophilisate | ≥95.0% |
| PSMA-T3 | $C_{35}H_{47}N_9O_{10}$; 753.34 g/mol; m/z = 754.35[M + H]$^+$ | water: insoluble pH 7.4 phosphte buffer: very slightly soluble ethanol: soluble | White lyophilisate | ≥97.0% |
| PSMA-T4 | $C_{37}H_{49}N_9O_{10}$; 779.36 g/mol; m/z = 780.31[M + H]$^+$ | water: practicaly insoluble pH 7.4 phosphte buffer: very slightly soluble ethanol: soluble | White lyophilisate | ≥97.0% |

Example 3. PSMA-T4
(PSMA-LTrp-4Amc-HYNIC) Hydrazone Synthesis wherein:
R=$R^1$, $R^2$, $R^3$, $R^4$, $R^5$=H, X, $CH_3$, $(CH_2)_nCH_3$, $OCH_3$, $O(CH_2)_nCH_3$, OH, $NO_2$, $NHCH_3$, $N(CH_3)_2$, $(CH_2)_nNCH_3$, $(CH_2)_nN(CH_3)_2$, $CF_3$, $OCF_3$, $SCH_3$, $SO_3Na$, $SO_3K$, $SO_2CH_3$, COOH, COONa, COOK, $(CH_2)_nCOOH$, $(CH_2)_n$COONa, $(CH_2)_nCOOK$, CN X=Cl, Br, I, F or wherein:
$R^1$=H, $CH_3$, $(CH_2)_nCH_3$, $(CH_2)_nCH_2OH$, $(CH_2)_nCH_2NO_2$, $(CH_2)_nCH_2N(CH_3)_2$, $(CH_2)_nCH_2X$, $(CH_2)_nCHO$, $CHOCH_3$, $(CH_2)_nCHOCH_3$ X=Cl, Br, I, F Crude, unpurified PSMA-T4 inhibitor is used for hydrazone synthesis. The compound is dissolved in water/ethanol solution and alcohol solution of suitable aldehyde is added in tenfold molar excess in relation to the inhibitor. The reaction is carried out for 10 to 20 minutes in room temperature depending on the aldehyde used. The reaction mixture comprising 4-(dimethylaminebenzo)hydrazone of PSMA-T4 is purified on a preparative polymeric HPLC reversed phase column. Collected PSMA-T4 hydrazone fractions fulfilling the purity requirements are combined and lyophilized. The applied modification according to the invention allows to obtain the compound whose retention time differs significantly from the one for PSMA-T4 and the majority of the impurities difficult to separate in the case of unmodified peptide. This simplifies the purification process of hydrazone derivatives and enhances its yield. Obtained compounds exhibit high purity, i.e. above 99%, and higher stability in solutions. For example, 4-(dimethylaminebenzeno)hydrazone of PSMA-T4 was stable in the pH=7 phosphate buffer solution at least for a day.

Examples of PSMA-T4 hydrazones and their physicochemical characteristics are presented in Table 2.

TABLE 2

Physicochemical data of chosen hydrazones of PSMA-T4 compound

| Compound | Molecular formula; $M_{cz}$; MS: m/z | Solubility according to Ph. Eur. | Form | HPLC purity |
|---|---|---|---|---|
| Benzenesulfonic acid hydrazone of PSMA-T4 | $C_{44}H_{53}N_9O_{13}S$; 948.00 g/mol; m/z = 948.35 $[M + H]^+$ | water: soluble pH 7.4 phosphte buffer: soluble ethanol: soluble | White or slightly yellow lyophilizate | ≥97.0% |
| 4-(dimethylaminebenzene) hydrazone of PSMA-T4 | $C_{46}H_{58}N_{10}O_{10}$; 911.01 g/mol; m/z = 911.44 $[M + H]^+$ | water: practicaly insoluble pH 7.4 phosphte buffer: soluble ethanol: soluble | yellow lyophilizate | ≥99% |
| Vanilin hydrazine of PSMA-T4 | $C_{45}H_{55}N_9O_{12}$; M = 913.97 g/mol; m/z = 914.40 $[M + H]^+$ | water: practicaly insoluble pH 7.4 phosphte buffer: slightly soluble ethanol: soluble | White lyophilizate | ≥97.0% |

Example 4. Preparation of Radiopharmaceutical Kit for Preparing $^{99m}$Tc-HYNIC-PSMA The pharmaceutical kit according to the invention comprises a dry composition of ingredients necessary for labelling with Technetium-99m, sealed under nitrogen atmosphere. The dry composition comprises PSMA inhibitor according to the invention, for instance PSMA-T4 compound or its hydrazone derivative, reducing agent $SnCl_2 \times 2 H_2O$, coligands for obtaining a stable complex with radiometal: tricine and ethylenediamine-(N,N')-diacetic acid (EDDA) as well as phosphate buffer for pH adjusting.

As part of the pharmaceutical method for preparation of the kit, in order to obtain the dry composition, 0.1 M pH 7.4 phosphate buffer solution is prepared, in which the solution of PSMA-T4 or its hydrazone derivative at the concentration of 0.01 μM to 0.05 μM, tricine at the concentration of 0.06 mM to 0.56 mM, EDDA at the concentration of 0.03 mM to 0.09 mM is prepared. The solution prepared in such a way is purged with gaseous nitrogen and then the solution of 0.1 μM to 0.4 μM $SnCl_2 \times 2H_2O$ in the 0.1 M to 0.5 M hydrochloric acid is added. The solution is then filtered through the 0.22 μm antimicrobial filter and dispensed into 1 mL portions in glass vials and freezed. Next, the freeze-drying process is carried out. After the freeze-drying is finished, the lyophilizer chamber containing the vials is filled with nitrogen and inside the chamber, the vials are sealed with stoppers and after their removal from the chamber they are also sealed with metal caps to prevent them from unsealing. In such a way, a sterile and free of bacterial endotoxins radiopharmaceutical kit of the following exemplary composition is prepared:
PSMA-T4 or its hydrazone derivative 20 μg
Tricine 50 mg
EDDA 5 mg
$SnCl_2 \times 2H_2O$ 40 μg
$Na_2HPO_4 \times 12H_2O$ 29 mg
$NaH_2PO_4 \times 2H_2O$ 3.0 mg.

Figure 1:
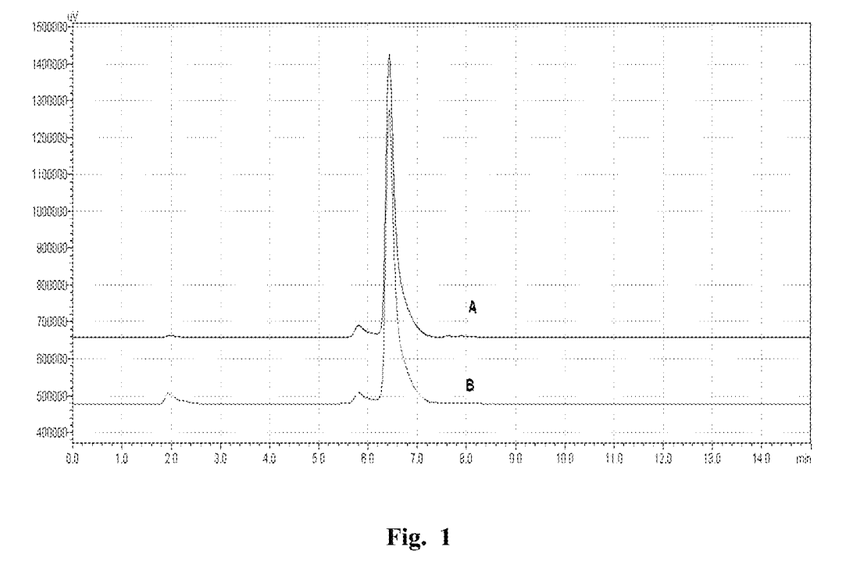
FIG. 1 shows radiochromatograms of HPLC: A—$^{99m}Tc$-PSMA-T4; B—$^{99m}Tc$-4 PSMA-T4-(dimethylaminebenzen)hydrazone.
Figure 2:
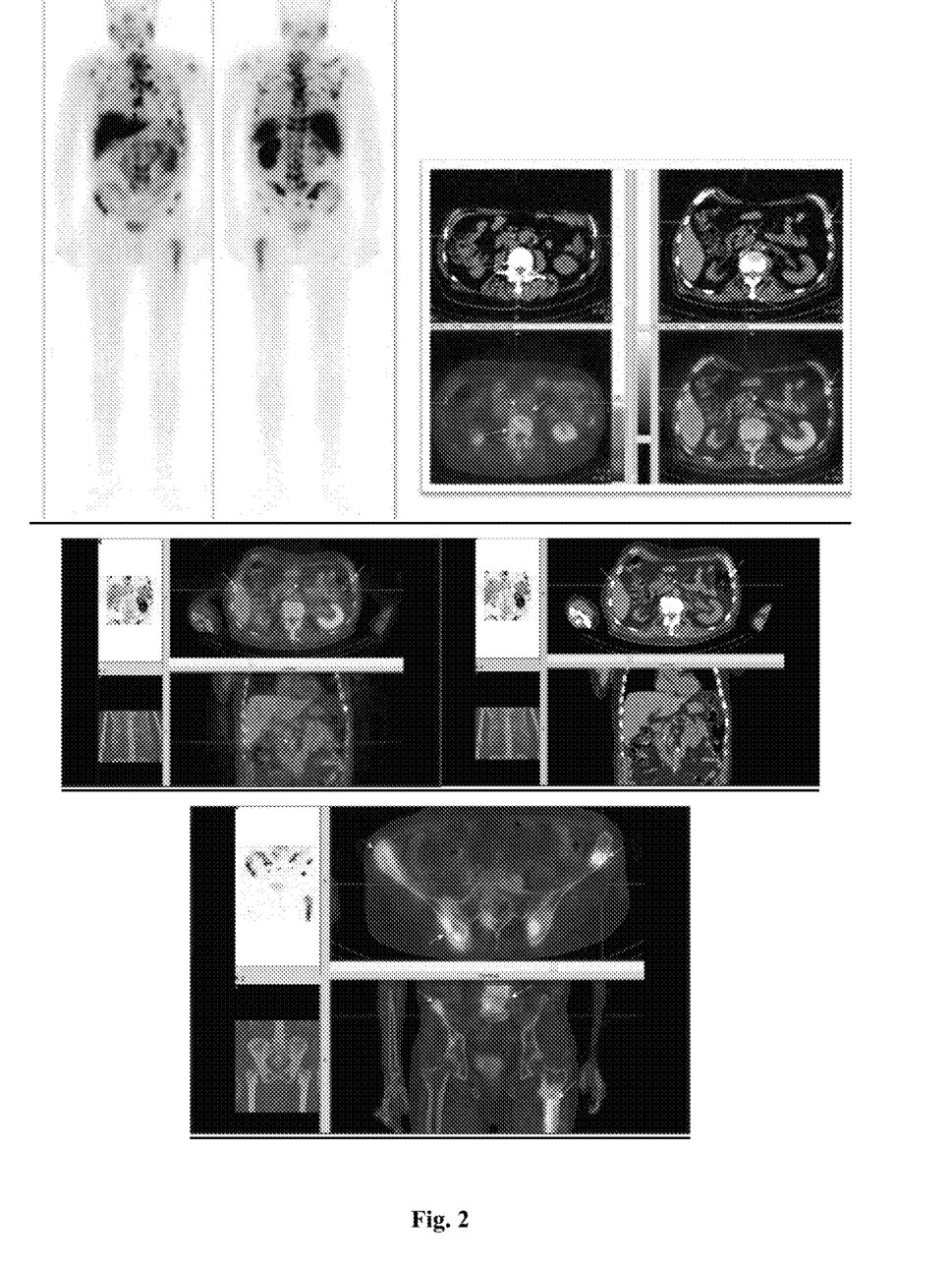
FIG. 2 shows the body scan and target SPECT-CT imaging with numerous visible metastases to the lymph nodes, bones and the abdominal cavity with intense radiopharmaceutical uptake.

As part of the method for obtaining radiopharmaceutical preparation with the use of the kit containing the above-mentioned composition, 0.5-2.5 mL of sodium pertechnetate $Na^{99m}TcO_4$ solution of required radioactivity (300-1500 MBq) is introduced to the vial containing the dry composition. After dissolving, the solution is heated at 100° C. for 15-30 minutes and then cooled down in room temperature for 20 minutes. Radiochemical purity of the preparation obtained in such a way and assessed with thin layer chromatography is above 90%. The radiopharmaceutical preparations obtained as a result of Technetium-99m labelling of PSMA-T4 and its hydrazone derivatives are identical as it has been confirmed by HPLC and LC/MS methods (see FIG. 1).

Example 5. Biological Activity In Vitro

An important advantage of the compounds described herein is their high affinity to the PSMA receptor present on prostate cancer cells. Competition ligand binding in vitro studies carried out on LNCaP carcinoma cell membranes allowed for determination of IC50 values, namely the concentrations at which the dissociation equilibrium is maintained. The studies were carried out using 96-well plates equipped with filters, to which the identical amount of membranes was applied. Next, increasing concentrations of inactive formulations and active competitive $^{131}$I-MIP1095 of high receptor affinity were added. After 2-hour incubation, the filters were washed and radioactivity was measured. IC50 values were determined using GraphPad Prism 7.0 statistics software.

In the course of the studies, IC50 values for the compounds according to the invention were from 75 nM to 97 nM respectively, which means that the compounds according to the invention have over 7 times higher affinity as compared to the commonly available tracer for prostate cancer diagnostics—PSMA 11 (Table 3).

TABLE 3

In vitro comparison of PSMA-T1, PSMA-T2, PSMA-T3, PSMA-T4 and PSMA 11 affinity to PSMA receptor.

|  | PSMA 11 | PSMA-T1 (PSMA-Nal-Amc-HYNIC) | PSMA-T2 (PSMA-Nal-AHX-HYNIC) | PSMA-T3 (PSMA-Trp-AHX-HYNIC) | PSMA-T4 (PSMA-Trp-Amc-HYNIC) |
|---|---|---|---|---|---|
| IC50 [nM] | 719 | 97 | 143 | 75 | 80 |
| $R^2$ | 0.956 | 0.963 | 0.926 | 0.984 | 0.972 |

Example 6. Biodistribution of PSMA Preparations Labelled with Technetium-99m

In comparative biodistribution studies on three PSMA preparations labelled with 99mTc, healthy BALB/c mice (males with body weight of 18-27 g) were used. 0.1 mL preparations with the activity of around 6 MBq were administered to the tail vein. After 4 hours of p.i.v. administration, animals were subjected to inhalation euthanasia and then required organs were collected and weighted, and the radioactivity accumulated therein was measured. Preparation accumulation in selected organs or tissues is given as % ID (percentage of injected dose) and % ID/g (percentage of injected dose per gram of the organ or tissue). Biodistribution data in Table 4 indicate that the critical organ for Technetium PSMA preparations is kidneys, wherein the retention levels of radioactivity in kidneys after administration of preparations based on PSMA-T3 and PSMA-T4 analogues were significantly lower than in the case of 99mTc-iPSMA reference preparation.

TABLE 4

| Biodistribution data | | | | | | | | | | | | |
|---|---|---|---|---|---|---|---|---|---|---|---|---|
| | $^{99m}$Tc-iPSMA 4 h p.i.v. mice n = 3 (mass 22.6 g ± 4.2 g) | | | | $^{99m}$Tc-PSMA-T1 4 h p.i.v. mice n = 3 (mass 26.1 g ± 6.6 g) | | | | $^{99m}$Tc-PSMA-T2 4 h p.i.v. mice n = 3 (mass 26.6 g ± 2.5 g) | | | |
| Organ | % ID | SD | % ID/g | SD | % ID | SD | % ID/g | SD | % ID | SD | % ID/g | SD |
| blood | | | 0.35 | 0.11 | | | 0.30 | 0.06 | | | 0.43 | 0.12 |
| thyroid | 0.10 | 0.04 | 0.73 | 0.38 | 0.10 | 0.04 | 0.64 | 0.22 | 0.17 | 0.03 | 0.94 | 0.24 |
| heart | 0.04 | 0.01 | 0.35 | 0.15 | 0.02 | 0.00 | 0.15 | 0.07 | 0.04 | 0.01 | 0.27 | 0.08 |
| lungs | 0.10 | 0.03 | 0.55 | 0.17 | 0.10 | 0.06 | 0.53 | 0.21 | 0.11 | 0.02 | 0.72 | 0.26 |

TABLE 4-continued

Biodistribution data

| Organ | | | | | | | | | | | | |
|---|---|---|---|---|---|---|---|---|---|---|---|---|
| liver | 0.57 | 0.06 | 0.50 | 0.18 | 0.63 | 0.48 | 0.43 | 0.24 | 0.77 | 0.22 | 0.53 | 0.11 |
| spleen | 0.23 | 0.05 | 1.33 | 0.45 | 0.61 | 0.60 | 1.62 | 1.83 | 0.37 | 0.19 | 1.72 | 0.50 |
| pancreas | 0.06 | 0.03 | 0.44 | 0.21 | 0.07 | 0.02 | 0.54 | 0.23 | 0.12 | 0.06 | 0.63 | 0.28 |
| kidneys | 65.75 | 23.44 | 190.64 | 113.13 | 57.60 | 12.57 | 159.27 | 71.09 | 67.72 | 4.66 | 156.05 | 28.41 |
| small intestine | 0.49 | 0.24 | 0.27 | 0.14 | 1.75 | 2.61 | 0.83 | 1.25 | 0.32 | 0.06 | 0.17 | 0.03 |
| large intestine | 1.20 | 0.94 | 1.23 | 0.98 | 0.50 | 0.20 | 0.39 | 0.07 | 1.39 | 0.27 | 0.97 | 0.05 |
| stomach | 0.06 | 0.02 | 0.34 | 0.10 | 0.12 | 0.13 | 0.62 | 0.70 | 0.09 | 0.02 | 0.38 | 0.10 |
| bone | | | 0.63 | 0.60 | | | 0.42 | 0.24 | | | 0.31 | 0.13 |
| muscle | | | 0.19 | 0.08 | | | 0.12 | 0.11 | | | 0.50 | 0.54 |
| urine | 26.83 | 24.37 | | | 33.77 | 12.71 | | | 20.68 | 5.54 | | |
| rest of body | 4.18 | 0.18 | | | 4.47 | 0.69 | | | 7.73 | 1.45 | | |

| | $^{99m}$Tc-PSMA-T3 4 h p.i.v. mice n = 3 (mass 24.2 g ± 3.9 g) | | | | $^{99m}$Tc-PSMA-T4 4 h p.i.v. mice n = 5 (mass 19 g ± 1.1 g) | | | |
|---|---|---|---|---|---|---|---|---|
| Organ | % ID | SD | % ID/g | SD | % ID | SD | % ID/g | SD |
| blood | | | 0.35 | 0.06 | | | 0.14 | 0.04 |
| thyroid | 0.36 | 0.23 | 2.04 | 1.26 | 0.00 | 0.00 | 0.14 | 0.15 |
| heart | 0.02 | 0.01 | 0.12 | 0.10 | 0.01 | 0.00 | 0.08 | 0.04 |
| lungs | 0.06 | 0.04 | 0.32 | 0.19 | 0.03 | 0.01 | 0.23 | 0.06 |
| liver | 0.98 | 0.30 | 0.68 | 0.18 | 0.12 | 0.04 | 0.12 | 0.04 |
| spleen | 0.18 | 0.18 | 0.58 | 0.42 | 0.04 | 0.02 | 0.27 | 0.11 |
| pancreas | 0.04 | 0.02 | 0.31 | 0.23 | 0.02 | 0.01 | 0.30 | 0.08 |
| kidneys | 23.05 | 9.05 | 60.37 | 29.88 | 9.92 | 2.36 | 37.54 | 9.40 |
| small intestine | 0.91 | 0.92 | 0.59 | 0.58 | 0.19 | 0.06 | 0.12 | 0.05 |
| large intestine | 0.99 | 0.31 | 0.78 | 0.20 | 0.86 | 1.00 | 0.84 | 0.95 |
| stomach | 0.18 | 0.14 | 1.04 | 0.95 | 0.01 | 0.01 | 0.12 | 0.03 |
| bone | | | 0.27 | 0.01 | 0.00 | 0.00 | 0.15 | 0.12 |
| muscle | | | 0.05 | 0.03 | | | 0.07 | 0.05 |
| urine | 67.90 | 11.46 | | | 86.64 | 2.86 | | |
| rest of body | 5.04 | 1.64 | | | 2.05 | 0.70 | | |

Example 7. Clinical Application of PSMA-T4 Labelled with Technetium-99m

SPECT-CT study was carried out 1-3 hours after intravenous administration of 99mTc-PSMA-T4 preparation according to the invention to 9 patients with prostate cancer. Imaging was performed using gamma camera SPECT-CT Symbia T2, Siemens. 9 patients post prostate cancer radical therapy (total prostatectomy or final radiotherapy) were enrolled in the studies. Patients with biochemical progress and clinical data concerning the disease relapse were examined for disease recurrence. Proper biodistribution of radiopharmaceuticals with high activity was observed in the liver, spleen, kidneys, salivary glands, intestine and bladder. In 7 patients, a local relapse was observed, metastases to lymph nodes and/or bones with intense tracer uptake. In 2 patients with a negative MRI result, a local relapse was suspected.

REFERENCES

[1] Sweat S D, Pacelli A, Murphy G P, Bostwick D G. Prostate-specific membrane antigen expression is greatest in prostate adenocarcinoma and lymph node metastases. Urology. 1998; 52(4):637-40.

[2] Banerjee S R, Foss C A, Castanares M, et al. Synthesis and evaluation of technetium-99m- and rhenium-labeled inhibitors of the prostate-specific membrane antigen (PSMA). J Med Chem. 2008; 51:4504-4517.

[3] Kularatne S A, Zhou Z, Yang J, Post C B, Low P S. Design, synthesis, and preclinical evaluation of prostate-specific membrane antigen targeted 99mTc-radioimaging agents. Mol Pharm. 2009; 6:790-800.

[4] Xiaoping Xu, et al. 99mTc-labeling and evaluation of a HYNIC modified small-molecular inhibitor of prostate-specific membrane antigen. Nucl. Med. Biol. 2017; 48:69-75.

[5] Guillermina Ferro-Flores, et al. Clinical translation of a PSMA inhibitor for 99mTc-based SPECT. Nucl. Med. Biol. 2017; 48:36-44.

[6] Robu S, Schottelius M, Eiber M, Maurer T, Gschwend J, Schwaiger M, Wester H J. Preclinical Evaluation and First Patient Application of 99mTc-PSMA-I&S for SPECT Imaging and Radioguided Surgery in Prostate Cancer. J Nucl Med. 2017, 58(2):235-242.

[7] Chan W. C., White P. D. Fmoc Solid Phase Peptide Synthesis. A practical approach. 2004, 47-48.

[8] El-Faham A., Albericio F., COMU: A third generation of uranium-type coupling reagents. Journal of Peptide Science. 2010, 16: 6-9.

[9] Subiros-Funosas R., L. Nieto-Rodriguez L., Jensen K. J., Albericio F., COMU: scope and limitations of the latest innovation in peptide acyl transfer reagents. Journal of Peptide Science. 2010, 16: 408-414.

[10] Chan W. C., White P. D. Fmoc Solid Phase Peptide Synthesis. A practical approach. 2004, 51.

The invention claimed is:

1. A compound comprising PSMA-HYNIC inhibitor derivatives selected from the group consisting of general formula 1:

Formula 1

(PSMA-L₁—L₂-HYNIC)

wherein: $L_1$=L-Trp (L-tryptophan), and $L_2$=6Ahx (6-aminohexanoic acid), 4Amc (4-aminomethylcyclohexane carboxylic acid) and their pharmaceutically acceptable salts, and aromatic hydrazone derivatives of general formula 3:

Formula 3

(PMSA-L₁-L₂-HYNIC-aromatic hydrazone)

wherein:

$L_1$=L-Trp (L-Tryptophan) and $L_2$=6Ahx (6-aminohexanoic acid), 4Amc (4-aminomethylcyclohexane carboxylic acid);

$R^1$, $R^2$, $R^3$, $R^4$, and $R^5$ are each selected from the group consisting of COOH, and CO3H" has been replaced with the phrase —H, $OCH_3$, OH, $N(CH_3)_2$, COOH, and $CO_3H$;

X=Cl, Br, I, or F;

and their pharmaceutically acceptable salts.

2. The compound as defined in claim 1 for use in scintigraphy diagnostics of prostate cancer and its metastasis.

3. A radiopharmaceutical preparation comprising the compound defined in claim 1, which is linked via chemical bond to a $^{99m}$Tc isotope.

4. A single vial radiopharmaceutical kit for labelling with a $^{99m}$Tc isotope comprising the compound defined in claim 1, and excipients chosen from the group consisting of tin(II) chloride, tricine, ethylenediamine-N,N'-diacetic acid (EDDA) and phosphate buffer.

5. The kit according to claim 4 wherein the compound and excipients are in sterile lyophilisate form under an inert gas atmosphere.

6. A method for preparing a radiopharmaceutical preparation, the method comprising the steps of:

1) adding a sodium pertechnetate Na$^{99m}$TcO$_4$ solution to the single vial radiopharmaceutical kit of claim 4;

2) followed by 15-30 minute incubation at 100° C.

\* \* \* \* \*